United States Patent [19]
Danner

[11] 3,991,302
[45] Nov. 9, 1976

[54] METHOD FOR DETECTING AND ISOLATING FAULTS IN DIGITAL AND ANALOG CIRCUITS WITH MULTIPLE INFRARED SCANNING UNDER CONDITIONS OF DIFFERENT STIMULI

[75] Inventor: Frederick G. Danner, Huntington, N.Y.

[73] Assignee: Grumman Aerospace Corporation, Bethpage, N.Y.

[22] Filed: Nov. 22, 1974

[21] Appl. No.: 526,301

[52] U.S. Cl. .................. 235/151.31; 324/73 PC; 250/338; 340/228 R
[51] Int. Cl.² .................. G01J 5/10; G01R 31/28
[58] Field of Search ......... 324/73 R, 73 AT, 73 PC; 250/338, 342; 73/355 R, 355 EM; 235/151.3, 151.35, 151.31; 340/228 R

[56] References Cited
UNITED STATES PATENTS

| | | | |
|---|---|---|---|
| 3,350,702 | 10/1967 | Herman | 340/228 |
| 3,463,007 | 8/1969 | Jones et al. | 324/73 X |
| 3,868,508 | 2/1975 | Lloyd | 250/338 X |

OTHER PUBLICATIONS

Infrared Microscopy for the Determination of the Initial State of an Integrated Circuit, M. Feuer & P. Goel; IBM Technical Disclosure Bulletin, vol. 15, No. 11, Apr. 1973, p. 3376.

Infrared as a Thermal Analysis Tool; M. L. Rauhe & H. E. Randall, Solid State Technology, Mar. 1970, pp. 67–72 and 87.

Primary Examiner—Edward J. Wise
Attorney, Agent, or Firm—Morgan, Finnegan, Pine, Foley & Lee

[57] ABSTRACT

A method for detecting faults in digital and analog circuits including the steps of thermally stabilizing the circuit, applying electrical stimulus to the circuit for a predetermined time period, scanning the circuit to determine the infrared response, applying another desired electrical stimulus to the circuit for a predetermined time period, scanning the circuit to determine the infrared response, repeating the applying and scanning sequence as desired, and comparing the resulting infrared responses with normal infrared profiles to detect and isolate faults in the circuit.

13 Claims, 5 Drawing Figures

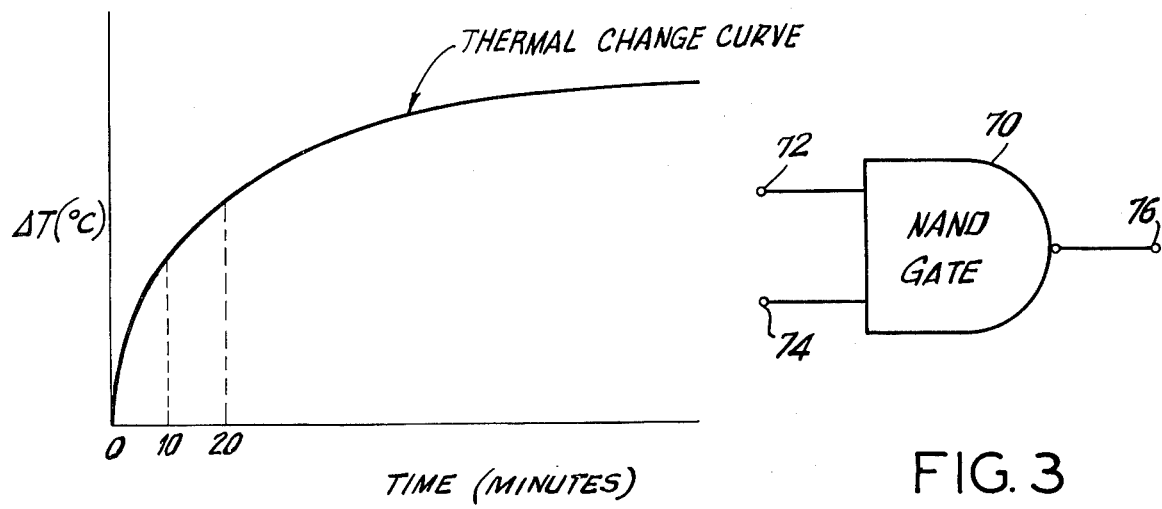
FIG. 2
FIG. 3
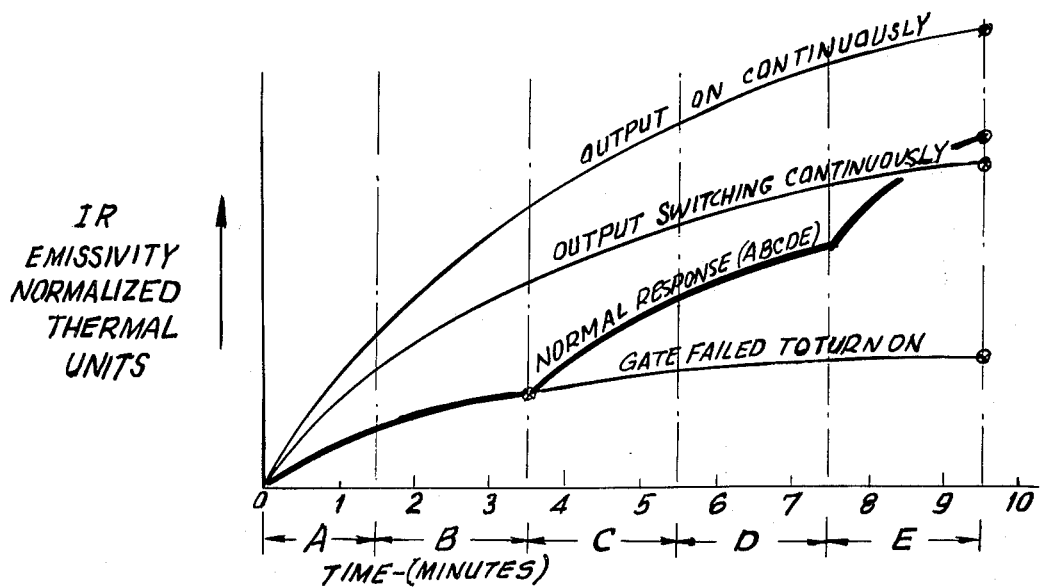
FIG. 4
FIG. 5 POSSIBLE IR RESPONSE CURVES

METHOD FOR DETECTING AND ISOLATING FAULTS IN DIGITAL AND ANALOG CIRCUITS WITH MULTIPLE INFRARED SCANNING UNDER CONDITIONS OF DIFFERENT STIMULI

The present invention relates to a method for detecting and isolating faults in digital and analog circuits, and more particularly to a method for detecting an isolating faults in digital and analog circuits with multiple infrared scanning under conditions of different stimuli.

It is known in the art to employ infrared radiometers to detect faults in printed circuit boards by using a single scan. Such known single scan techniques are generally accomplished in one of the following ways:

1. The circuit under test is electrically stimulated and a single infrared scan is made;
2. The circuit under test is stimulated dynamically to cause all of the circuit elements to switch simultaneously, and a single infrared scan is made;
3. The circuit under test is stimulated by a digital word generator with a large number of possible electrical input patterns, and a single infrared scan is made while these changing input patterns are being delivered to the circuit; or
4. The circuit under test is stimulated electrically until it is heated to a stable temperature value, and a single infrared scan is made.

Examples of such known infrared scanning techniques are disclosed in U.S. Pat. No. 3,350,702 (Jones et al.) and U.S. Pat. No. 3,463,007 (Herman).

All of these aforementioned techniques have been less than satisfactory in detecting and isolating a high percentage of faults.

It is an object of the present invention to provide an improved infrared scanning method for detecting and isolating faults in digital and analog circuits.

It is a still further object of the present invention to provide an improved infrared scanning method for detecting and isolating faults in complex digital and analog circuits.

It is a further object of the present invention to provide an improved infrared scanning method for detecting and isolating faults in integrated circuits.

It is a still further object of the present invention to provide an improved infrared scanning method for detecting and isolating faults in digital and analog circuits by a sequence of stimulus patterns to localize and identify the faults.

It is a still further object of the present invention to provide an improved method for infrared scanning which does not require thermal re-stabilization after each scan.

Other objects, aspects, and advantages of the present invention will be apparent when the detailed description is considered with the drawings.

Briefly, the present method for detecting and isolating faults in digital and analog circuits includes the steps of thermally stabilizing the circuit, applying a desired electrical stimulus to the circuit for a predetermined time period, scanning the circuit to determine its infrared response, applying another desired electrical stimulus to the circuit for a predetermined time period, scanning the circuit to determine its infrared response, repeating the applying and scanning sequence as desired, and comparing the resulting infrared responses from the multiple scans with previously stored normal infrared values to detect and isolate faults in the circuit.

The present invention is illustrated with reference to the accompanying drawings, in which:

FIG. 2 is a graph illustrating the general shape of the thermal change curve for a test circuit;

FIG. 3 is a NAND gate;

FIG. 4 is a partial infrared truth table for the NAND gate of FIG. 3; and

FIG. 5 is a graph showing the various possible infrared profiles or responses resulting from the partial truth table of FIG. 4 applied to the NAND gate of FIG. 3, including the normal infrared profile.

Figure 1:
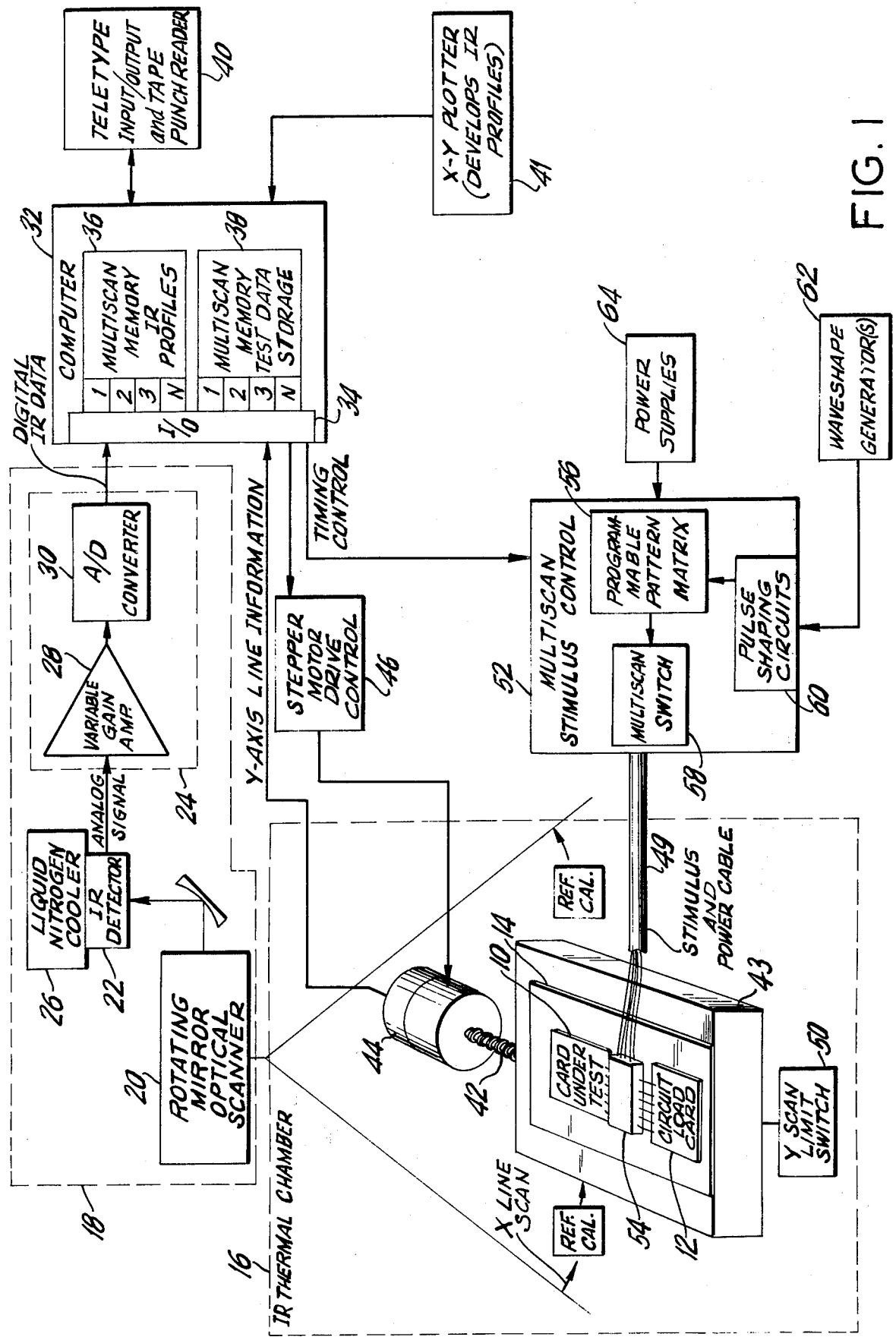
FIG. 1 is a block diagram of a system for carrying out the method of the present invention.

Referring to FIG. 1, the method of the present invention is being used to test a printed circuit card 10. However, it should be understood that the method of the present invention may be used with any analog and digital circuits, including integrated circuits. The printed circuit card 10 along with a circuit load card 12 is positioned on a positioner card 14 located in an infrared thermal chamber 16. A radiometer, generally located at 18, includes a rotating mirror optical scanner 20, an infrared detector 22 and signal processing electronics 24. The infrared detector 22 is cooled via a liquid nitrogen cooler 26. The signal processing electronics 24 include a variable gain amplifier 28 and a A/D converter 30. The infrared thermal chamber 16 and radiometer 18 are commercially available from Vanzetti Infrared And Computer Systems, Inc.

A general purpose digital computer 32, e.g., a Data General 800 or 1200 Series Computer or a Digital Equipment Corp. PDP-11 Series Computer, is electrically connected to the signal processing electronics 24 through an I/0 interface 34 to receive digital data from the A/D converter 30. The computer 32 includes a memory 36 for storing a plurality of normal infrared scan profiles (expected digital values), and a memory 38 for the test data resulting from the card 10. In both cases this data results from the application of appropriate stimuli from the multiscan stimulus control 52.

A teletype I/O and tape punch reader 40 or other data input device is electrically connected to the computer 32. Further, an X-Y plotter 41 is electrically connected to the computer 32 for developing the position of each of the test point locations. Such an X-Y position plotter is commerically available from Vanzetti Infrared And Computer Systems, Inc.

An X-Y axis precision positioning table 43 supports the positioner card 14 and is mechanically coupled to a worm gear 42. The positioner card 14 and table 43 are moved via the worm gear 42 which is coupled to a stepping motor/encoder 44 for transmitting Y-axis information to the I/O interface 34 of the computer 32. The stepping motor of the stepping motor/encoder 44 is controlled by a stepper motor drive control 46 which is electrically coupled to the I/O interface 34 of the computer 32. A Y-scan limit switch 50 establishes the reset position for the table 43 in the Y direction.

A multiscan stimulus control 52 is electrically connected to the circuit load card 12 and printed circuit card 10 through lead terminal 54. The multiscan stimulus control 52 includes a programmable pattern matrix 56, which may advantageously be included as part of the computer 32, a multiscan switch 58, and pulse shaping circuits 60 which provide inputs to the programmable pattern matrix 56. A wave shape generator(s) 62 activates the pulse shaping circuits 60. Power supplies 64 are connected to the cards 10 and 12 via the multiscan stimulus control 52. A timing control signal from the I/O interface 34 of the computer 32 controls activation of the multiscan stimulus control 52.

For operation of the system shown in FIG. 1, the electronic circuitry on the printed circuit card 10 (or other two dimensional chassis) and the load components on card 12 are positioned on the positioner card 14. The card 14, along with cards 10 and 12, is initially placed on an X-Y positioning table in the X-Y plotter 41. The X-Y positioning table 43 in the X-Y plotter 41 is identical to the X-Y positioning table 43 in the infrared thermal chamber 16. In the X-Y plotter 41, fibre optics (not shown) vertically determine each test point location on the cards 10 and 12 where infrared data is to be recorded. X-Y digital line encoders on the X-Y plotter 41 convert the output of the fiber optics to X and Y coordinates for each desired test point location, generally within 50 milliinch increments. The X and Y corrdinates for the desired test points are transmitted to the computer 32 and stored in memories 36 and 38.

Sets of expected data values or patterns for the infrared test points are programmed into the computer 32 and stored in locations of the memory 36. Depending on the size of the memory 36, and the type of general purpose computer 32 used, any number of patterns can be stored in the computer 32, e.g., 1, 2, 3 . . . N.

After the desired number of infrared test points are developed by the X-Y plotter 41 and the X-Y locations for all the test points of these patterns are stored in the memories 36 and 38, the card 14, along with cards 10 and 12, is positioned on the X-Y positioning table 43 located in the chamber 16. A stimulus and power cable 49 couples the multiscan stimulus control 52 to the lead terminal 54 and transmits dynamic electrical signals and power supply voltages from the multiscan stimulus control 52 to the cards 10 and 12 or portions thereof.

Initially, to provide thermal stabilization, an infrared scan is made, without any electrical stimulus applied to the cards 10 and 12, to determine that the temperature of the cards 10 and 12 is substantially at ambient room temperature. Advantageously, initial stabilization may be expedited by recording initial stabilization values close to the ambient temperature and substracting these values from subsequent test data values, thereby normalizing the test data.

After the initialization conditions are determined, stimulus signals and power signals corresponding to the first desired electrical stimulus are transmitted to the test card 10 and load card 12 from the multiscan stimulus control 52 for a predetermined time period, typically selected between about 5 seconds to about 4 minutes, to increase the temperature of the circuit pior to scanning. At the end of the period for the first desired stimulus pattern, an infrared scan is initiated by the teletype I/O 40 and infrared data is collected for all the test points and stored in location 1 of the memory 38 of the computer 32.

Under influence of timing control signals from the computer 32, the multiscan stimulus control 52 switches to the second desired stimulus pattern and dynamically heats the test circuit of cards 10 and 12 for a second time period. A second infrared scan is made at the end of the period for the second stimulus and infrared data is collected and stored in location 2 of the memory 38. It should be apparent several interim stimulus patterns may be used prior to reaching the next desired pattern. The subsequent print-out of processed data is used in conjunction with the electrical schematic of the cards 10 and 12 to determine the fault(s). This stimulusscan sequence is repeated for as many different patterns as is necessary to produce the required number of logical variations for providing data to isolate all open, short, or non-functioning component faults. Post-processing of the test data includes comparing the stored test data in memory 38 with the expected or normal infrared values previously stored in the memory 36 of the computer 32.

During the infrared scanning operation, the card 14 is moved along its Y-axis by the stepping motor 44 coupled to the worm gear 42. As each digital Y-line is reached where test points are located, the motor 44 stops and the rotating mirror optical scanner 20 completes an X-axis line scan across the circuit under test, see arrow in FIG. 1. The resulting analog infrared levels are detected by the cooled infrared detector 22 which develops a voltage signal proportional to the infrared emission level detected along the X-axis. The resulting analog voltage is amplified by amplifier 28 and converted to a digital signal in A/D converter 30. The computer 32 samples the output of the A/D converter 30 when the scanner 20 reaches one of the X-Y test points stored in the memory 36. The received digital data is stored in a corresponding memory location in the test data memory 38.

When all of the X points of interest on a Y-axis line have been sampled, the computer 32 signals the stepping motor drive control 46 to move the card 14 to the next Y line of interest. After data from all test points has been received the stepping motor 44 moves the X-Y table 43 to its reset position to ready the test circuit of the cards 10 and 12 for their next scan.

The multiscan stimulus control 52 transmits signals from the waveshape generators 62 and applies voltage levels to the test circuit of cards 10 and 12 in accordance with the predetermined programmed sequence of pattern matrix 56 to heat the circuit 10. Components which are open or shorted will not produce the "normal" IR signature response and therefore appear "hot" or "cold", enabling a circuit fault to be isolated.

Referring to FIG. 2, a typical thermal change curve for a circuit turned on at time T=O, is shown. The linear portion (first thermal time constant) of the thermal change curve lasts approximately 10 minutes. It is during this portion of the thermal change curve that the various electrical stimulus patterns are applied to the circuit and the various infrared scan profiles are taken. Once the thermal change curve flattens out, the infrared profile flattens out with the result that the infrared profile changes little under various electrical stimuli. Therefore, the data collected subsequent to the linear portion of the thermal change curve provides little useful information.

Referring to FIG. 3, a NAND gate 70 is illustrated. The NAND gate 70 includes a first input terminal or pin 72, a second input terminal or pin 74, and an output terminal or pin 76. The partial thermal truth table for the NAND gate 70 is illustrated in FIG. 4. To provide complete fault isolation with regard to the NAND gate 70 it is only necessary to logically exercise it in accordance with its partial truth table, i.e., so that its inputs and outputs are forced to all possible logic states. This is accomplished according to the method of the present invention as follows: The NAND gate 70 is initially stimulated (Case A), e.g., for 0 to 1.5 minutes, with first input terminal 72 receiving a low logic signal and second input terminal 74 receiving a positive square wave input. An infrared scan of the test circuit is then made. During the next sequence, e.g., from 1.5 to 3.5 minutes, the first input terminal 72 receives a positive square wave input and the second input terminal 74 receives a low logic signal. A second infrared scan is then made. During the next sequence, e.g., from 3.5 to 5.5 minutes the first input terminal 72 receives a high logic signal and the second input terminal 74 receives a positive square wave input. A third infrared scan is then made. During the next sequence, e.g., from 5.5 to 7.5 minutes, the first input terminal 72 receives a positive square wave input and the second input terminal 74 receives a high logic signal. A fourth infrared scan is then made. During the final sequence, e.g., from 7.5 to 9.5 minutes the input terminals 72 and 74 receive high logic signals. A fifth infrared scan is then made. The data from the five infrared scans is compared with normal infrared profile signatures to isolate a faulty gate.

Referring to FIG. 5, various possible infrared response curves for the logically exercised gate 70 are illustrated with the normal output response curve. The resulting infrared response curves will show a faulty gate and in which state the gate is faulty.

Thus, it is apparent from the foregoing description that the method of the present invention permits digital detection and isolation of faulty logical circuits by stimulating them in accordance with predetermined patterns and scanning the circuit after each change to a new desired stimulus pattern.

It should be apparent to those skilled in the art that various modifications may be made in the present invention without departing from the spirit and scope thereof, as described in the specification and defined in the appended claims.

What is claimed is:
1. A method for isolating faults in digitial and analog circuits during a single test sequence, comprising the steps of:
 a. initially thermally stabilizing a circuit to be fault tested;
 b. applying a first predetermined stimulus pattern to the circuit for a predetermined portion of the test sequence;
 c. scanning the circuit to detect its infrared response;
 d. applying a second predetermined stimulus pattern to the circuit for another predetermined portion of the test sequence subsequent to the scanning of the first predetermined stimulus pattern and absent any thermal re-stabilization prior to the application of the second stimulus pattern;
 e. scanning the circuit to detect its infrared response; and
 f. analyzing the resulting infrared responses to detect and isolate faults in the circuit.

2. The method claimed in claim 1 including the steps of:
 successively repeating the stimulus applying and scanning steps, dependent upon the type of circuit being fault tested, with the absence of any thermal re-stabilization prior to the application of each predetermined stimulus pattern, to logically isolate the faults in the circuit.

3. The method in claim 1 wherein:
 the stimulus patterns are pre-programmed electrical signals which are applied to the circuit for predetermined portions of the test sequence.

4. The method claimed in claim 3 wherein:
 the pre-programmed electrical stimulus patterns exercise all the inputs of the circuit during the test sequence to produce all thermally significant outputs.

5. The method claimed in claim 1 including the step of:
 comparing the resulting infrared responses with normal infrared profiles to detect and isolate faults.

6. The method claimed in claim 1 wherein:
 the single test segment occurs within the linear portion of the thermal change curve for the circuit.

7. The method claimed in claim 1 including the steps of:
 storing normal infrared response data;
 storing the infrared response data resulting from the multiple scans of the circuit.

8. The method claimed in claim 1 including the step of:
 providing a number of stimulus patterns to exercise the circuit prior to the application of the next predetermined stimulus pattern.

9. A method for isolating faults in digital circuits during a single test sequence, comprising the steps of:
 a. initially thermally stabilizing a digital circuit to be fault tested;
 b. applying a predetermined stimulus pattern to the digital circuit for a predetermined time period;
 c. scanning the digital to detect its infrared response;
 d. repeating the stimulus applying and scanning steps (b) and (c) with different predetermined stimulus patterns and with the absence of any thermal re-stabilization prior to the application of each predetermined stimulus pattern so that the inputs and outputs of all thermally significant logical states of the digital circuit are exercised; and
 e. analyzing the resulting infrared responses to detect and isolate faults in the digitial circuit.

10. The method claimed in claim 9 wherein:
 the single test sequence occurs within the linear portion of the thermal change curve for the digital circuit.

11. The method claimed in claim 9 including the step of:
 storing normal infrared response data;
 storing the infrared response data resulting from the multiple scans of the digital circuit.

12. The method claimed in claim 9 including the step of:
 providing a number of stimulus patterns to exercise the digital circuit prior to the application of the next predetermined stimulus pattern.

13. A method for isolating substantially all open, short, and non-functioning circuit components in digital and analog circuits during a single test sequence, comprising the steps of:
 a. initially thermally stabilizing the circuit to be tested;
 b. applying a predetermined stimulus pattern to the circuit for a predetermined portion of the test sequence;
 c. scanning the circuit to detect its infrared response;
 d. repeating the stimulus applying and scanning steps (b) and (c) with different predetermined stimulus patterns and the absence of any thermal re-stabilization prior to application of each different predetermined stimulus pattern, until the inputs and outputs of all thermally significant states of the circuit have been exercised; and
 e. analyzing the resulting infrared responses to detect and isolate open, short, and non-functioning circuit components.

* * * * *